(12) United States Patent
Prevost et al.

(10) Patent No.: US 11,672,670 B2
(45) Date of Patent: *Jun. 13, 2023

(54) EXPANDABLE SPINAL IMPLANT SYSTEM AND METHOD

(71) Applicant: WARSAW ORTHOPEDIC INC., Warsaw, IN (US)

(72) Inventors: Julien Prevost, Memphis, TN (US); Robert Loke, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 497 days.

This patent is subject to a terminal disclaimer.

(21) Appl. No.: 16/853,573

(22) Filed: Apr. 20, 2020

(65) Prior Publication Data

US 2020/0261236 A1 Aug. 20, 2020

Related U.S. Application Data

(60) Continuation of application No. 15/830,652, filed on Dec. 4, 2017, now Pat. No. 10,675,155, which is a
(Continued)

(51) Int. Cl.
*A61F 2/44* (2006.01)
*A61F 2/30* (2006.01)
*A61F 2/28* (2006.01)

(52) U.S. Cl.
CPC .............. *A61F 2/44* (2013.01); *A61F 2/442* (2013.01); *A61F 2/4425* (2013.01);
(Continued)

(58) Field of Classification Search
CPC .......... A61F 2/44; A61F 2/442; A61F 2/4425; A61F 2/4455; A61F 2/30
See application file for complete search history.

(56) References Cited

U.S. PATENT DOCUMENTS 5,989,290 A * 11/1999 Biedermann ............. A61F 2/44
606/907
7,678,148 B2 3/2010 Peterman
(Continued)

FOREIGN PATENT DOCUMENTS

JP SHO 49-11836 3/1974
JP HEI 11-137585 5/1999
(Continued)

OTHER PUBLICATIONS

European Search Report for EP 13872936.3 date of completion is Aug. 10, 2016 (8 pages).
(Continued)

*Primary Examiner* — Christopher J Beccia
(74) *Attorney, Agent, or Firm* — Sorell, Lenna & Schmidt, LLP

(57) ABSTRACT

A spinal implant includes a first member having a wall that defines an axial cavity. A second member extends between a first end and a second end and defines a longitudinal axis. The second member is configured for disposal with the axial cavity and translation relative to the first member. A third member has an outer surface engageable with tissue and an inner surface disposed to dynamically engage the first end in response to the engagement of the outer surface with the tissue. Systems and methods are disclosed.

20 Claims, 10 Drawing Sheets

Related U.S. Application Data division of application No. 14/831,444, filed on Aug. 20, 2015, now Pat. No. 9,844,441, which is a division of application No. 13/749,354, filed on Jan. 24, 2013, now Pat. No. 9,138,324.

(52) U.S. Cl.
CPC ........ *A61F 2/4455* (2013.01); *A61F 2/30744* (2013.01); *A61F 2/30965* (2013.01); *A61F 2002/2817* (2013.01); *A61F 2002/2835* (2013.01); *A61F 2002/3008* (2013.01); *A61F 2002/3042* (2013.01); *A61F 2002/3055* (2013.01); *A61F 2002/30062* (2013.01); *A61F 2002/30064* (2013.01); *A61F 2002/30224* (2013.01); *A61F 2002/30225* (2013.01); *A61F 2002/30233* (2013.01); *A61F 2002/30235* (2013.01); *A61F 2002/30395* (2013.01); *A61F 2002/30401* (2013.01); *A61F 2002/30405* (2013.01); *A61F 2002/30484* (2013.01); *A61F 2002/30492* (2013.01); *A61F 2002/30495* (2013.01); *A61F 2002/30523* (2013.01); *A61F 2002/30538* (2013.01); *A61F 2002/30579* (2013.01); *A61F 2002/30593* (2013.01); *A61F 2002/30594* (2013.01); *A61F 2002/30601* (2013.01); *A61F 2002/30785* (2013.01); *A61F 2002/30836* (2013.01); *A61F 2002/30838* (2013.01); *A61F 2002/30841* (2013.01); *A61F 2002/30878* (2013.01); *A61F 2002/443* (2013.01); *A61F 2002/448* (2013.01); *A61F 2230/0069* (2013.01); *A61F 2310/00017* (2013.01); *A61F 2310/00023* (2013.01); *A61F 2310/00029* (2013.01); *A61F 2310/00077* (2013.01); *A61F 2310/00179* (2013.01); *A61F 2310/00293* (2013.01); *A61F 2310/00359* (2013.01)

(56) References Cited

U.S. PATENT DOCUMENTS

| | | | |
|---|---|---|---|
| 7,691,147 B2 * | 4/2010 | Gutlin | A61F 2/44 606/90 |
| 8,241,363 B2 | 8/2012 | Sommerich et al. | |
| 10,675,155 B2 * | 6/2020 | Prevost | A61F 2/4425 |
| 2006/0293755 A1 | 12/2006 | Lindner et al. | |
| 2008/0177387 A1 | 7/2008 | Parimore et al. | |
| 2009/0062862 A1 | 3/2009 | Perrow et al. | |
| 2010/0004746 A1 | 1/2010 | Arramon | |
| 2010/0179655 A1 | 7/2010 | Hansell et al. | |
| 2010/0324686 A1 | 12/2010 | Gerner | |
| 2010/0324687 A1 * | 12/2010 | Melkent | A61F 2/44 623/17.16 |
| 2011/0184523 A1 | 7/2011 | Blackwell et al. | |
| 2012/0179255 A1 | 7/2012 | Defalco et al. | |
| 2012/0239147 A1 | 9/2012 | Winkler | |
| 2014/0179255 A1 | 6/2014 | Drapkin et al. | |

FOREIGN PATENT DOCUMENTS

| | | |
|---|---|---|
| JP | 2008-536649 | 9/2008 |
| WO | WO 2006/116052 A2 | 11/2006 |

OTHER PUBLICATIONS

European Search Report for EP 17176110.9 date of completion is Oct. 18, 2017 (6 pages).
International Search Report for PCT/US2013/073065 date of completion is Mar. 6, 2014 (13 pages).

* cited by examiner

EXPANDABLE SPINAL IMPLANT SYSTEM AND METHOD

CROSS-REFERENCE TO RELATED APPLICATIONS

This application is a continuation of U.S. patent application Ser. No. 15/830,652, filed Dec. 4, 2017, which is a divisional application of U.S. patent application Ser. No. 14/831,444, filed Aug. 20, 2015, now U.S. Pat. No. 9,844,441, which is a divisional application of U.S. patent application Ser. No. 13/749,354, filed Jan. 24, 2013, now U.S. Pat. No. 9,138,324. These applications are expressly incorporated herein by reference, in their entireties.

TECHNICAL FIELD

The present disclosure generally relates to medical devices for the treatment of musculoskeletal disorders, and more particularly to a surgical system that includes an expandable spinal implant and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminectomy and implantable prosthetics. In procedures, such as, for example, corpectomy and discectomy, fusion and fixation treatments may be performed that employ implants to restore the mechanical support function of vertebrae. This disclosure describes an improvement over these prior art technologies.

SUMMARY

In one embodiment, in accordance with the principles of the present disclosure, a spinal implant is provided. The spinal implant comprises a first member having a wall that defines an axial cavity. A second member extends between a first end and a second end and defines a longitudinal axis. The second member is configured for disposal with the axial cavity and translation relative to the first member. A third member has an outer surface engageable with tissue and an inner surface disposed to dynamically engage the first end in response to the engagement of the outer surface with the tissue.

BRIEF DESCRIPTION OF THE DRAWINGS

The present disclosure will become more readily apparent from the specific description accompanied by the following drawings, in which.

DETAILED DESCRIPTION

Figure 1:
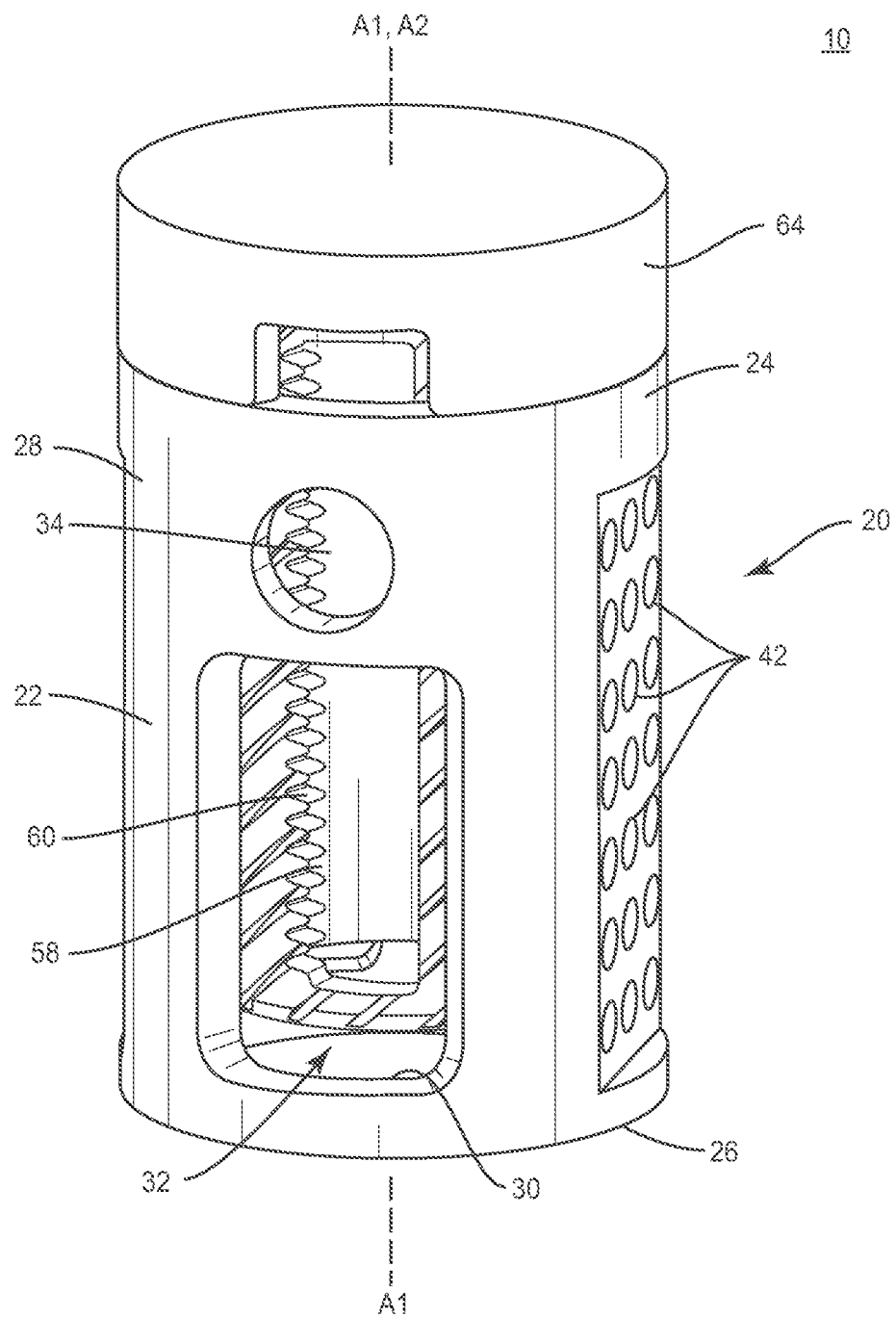
FIG. 1 is a perspective view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical system that includes an expandable spinal implant and a method for treating a spine.

In one embodiment, the surgical system includes an implant having at least one articulating end cap that adjusts to match the angle of vertebral endplates that the implant engages. In one embodiment, the endplates engage the implant such that the relative orientation of the endplates selectively determines an orientation, such as, for example a required angle, of the end caps for engagement with the endplates. This configuration provides engagement between the end cap and the vertebrae to facilitate distribution of a compressive load of vertebrae on the implant. In one embodiment, the articulating end caps accommodate for axial offset in a sagittal and/or a coronal plane of a body and allow the end caps to seat properly in the endplates. In some embodiments, this configuration resists and/or prevents a mismatch between the angle of the end caps and the angle between the cranial and caudal vertebral endplates. In some embodiments, this configuration resists and/or prevents point loading on the implant and eventual subsidence.

In one embodiment, the surgical system includes an implant having an articulating end cap for expandable vertebral body replacement implants. In one embodiment, the end cap includes a wedding cake configuration. In one embodiment, the wedding cake has a stepped profile on the top of the implant and a domed end cap. In one embodiment, the end cap includes a locking ring that allows the end cap to selectively and/or automatically settle on one or more of the wedding cake steps to accommodate the adjacent vertebral body. In one embodiment, the domed end cap is deformable for engagement with the stepped profile of the implant to provide a locking engagement of the implant between vertebral endplates. For example, under an axial compressive force, due for example from distraction forces or natural axial loading of a spine, the stepped wedding cake profile deforms and/or indents the domed end cap to lock the implant in a final configuration.

In one embodiment, the end cap includes a pin and set screw configuration that facilitates two distinct degrees of freedom to allow for articulation of the end cap relative to the end of the implant. In one embodiment, the implant includes a first degree of freedom that includes pivoting about an axis defined by the pin and set screw. In one embodiment, the implant includes a second degree of freedom, which includes the pin and set screws being set into a geometric configuration, such as, for example, circular, rectangular or square, and domed indentation or loose fit in the outer sidewall of the implant to allow for articulation. In one embodiment, the articulation can be limited by the size of the domed indentation. In some embodiments, the pin and/or setscrew tip can have various configurations, such as, for example, complimentary to the domed curvature corresponding to the indentation of the sidewall, or a rounded tip configured for single-point loading at the indentation of the sidewall. In one embodiment, the setscrew is configured to simplify assembly of the end cap onto an inner core of the implant and facilitate final tightening of the setscrew to lock the end cap in a final configuration.

In one embodiment, one or all of the components of the surgical system are disposable, peel-pack, pre-packed sterile devices used with an implant. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-6, there is illustrated components of a surgical system, such as, for example, a spinal implant system 10 in accordance with the principles of the present disclosure.

The components of spinal implant system 10 can be fabricated from biologically acceptable materials suitable for medical applications, including metals, synthetic polymers, ceramics and bone material and/or their composites, depending on the particular application and/or preference of a medical practitioner. For example, the components of spinal implant system 10, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a minimally invasive procedure, including percutaneous techniques, mini-open and open surgical techniques to deliver and introduce instrumentation and/or an implant, such as, for example, a corpectomy implant, at a surgical site within a body of a patient, for example, a section of a spine. In some embodiments, system 10 may be employed with surgical procedures, such as, for example, corpectomy and discectomy, which include fusion and/or fixation treatments that employ implants, in accordance with the principles of the present disclosure, to restore the mechanical support function of vertebrae.

System 10 includes an implant 20 having a first member, such as, for example, an outer body 22 having a tubular configuration. Body 22 extends between a first end 24 and a second end 26 and defines a longitudinal axis A1. End 26 defines a substantially planar surface that is configured to engage vertebral tissue. In some embodiments, end 26 can include a surface that may be rough, textured, porous, semi-porous, dimpled and/or polished such that it facilitates engagement with tissue. In some embodiments, the vertebral tissue may include intervertebral tissue, endplate surfaces and/or cortical bone.

Body 22 includes a wall, such as, for example, a tubular wall 28. Wall 28 includes an inner surface 30 that defines an axial cavity 32 extending between ends 24, 26. In some embodiments, wall 28 has a cylindrical cross-section. In some embodiments, the cross-section geometry of wall 28 may have various configurations, such as, for example, round, oval, oblong, triangular, polygonal having planar or arcuate side portions, irregular, uniform, non-uniform, consistent, variable, horseshoe shape, U-shape or kidney bean shape. In some embodiments, surface 30 is smooth or even. In some embodiments, surface 30 may be rough, textured, porous, semi-porous, dimpled and/or polished.

Wall 28 defines a lateral opening 34. Opening 34 is configured for disposal of an instrument I (FIG. 2) utilized to facilitate expansion of body 22 and a second member, such as, for example, an inner body 44 of implant 20, as described herein.

Figure 2:
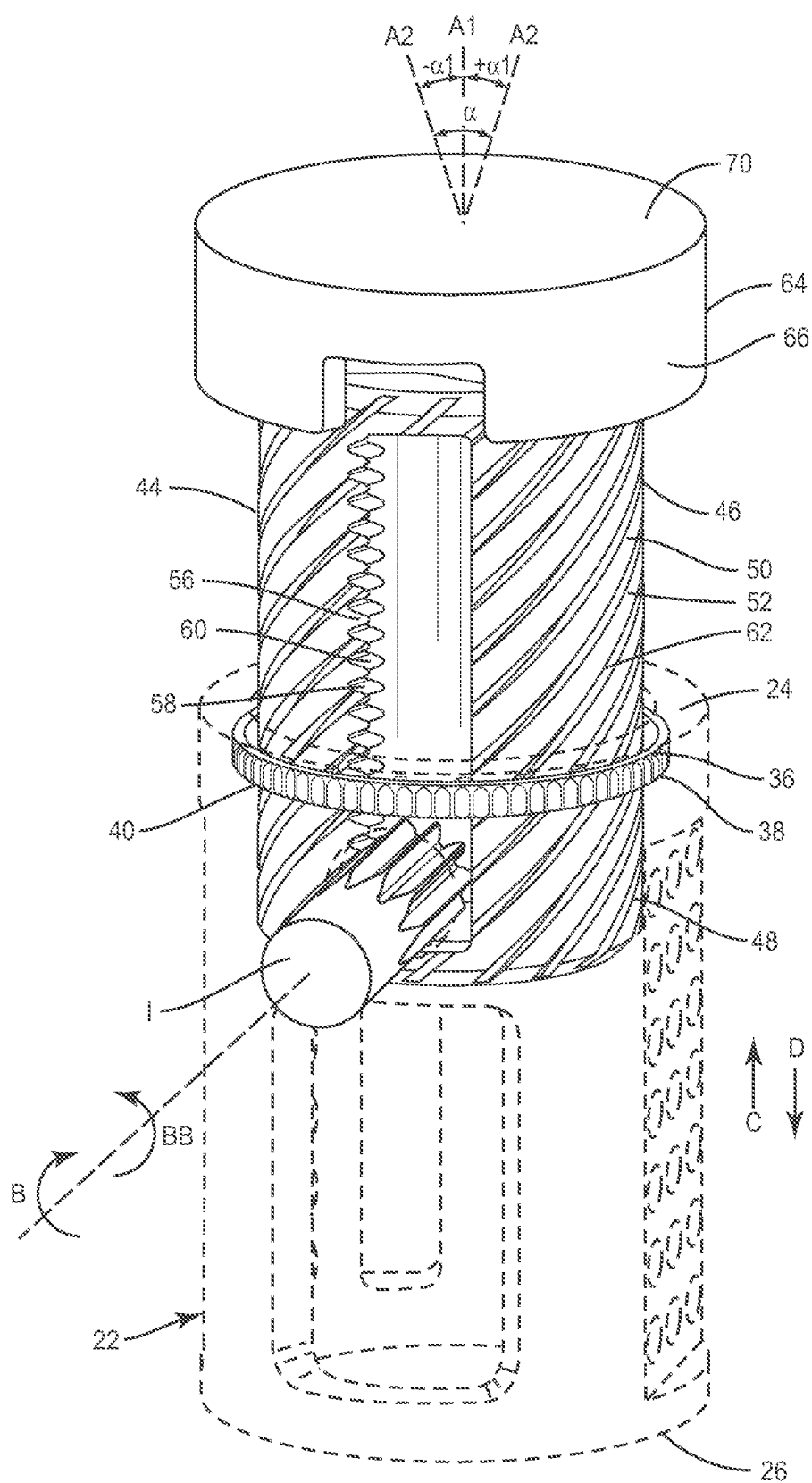
FIG. 2 is a perspective view of components of the system shown in FIG. 1.
Figure 3:
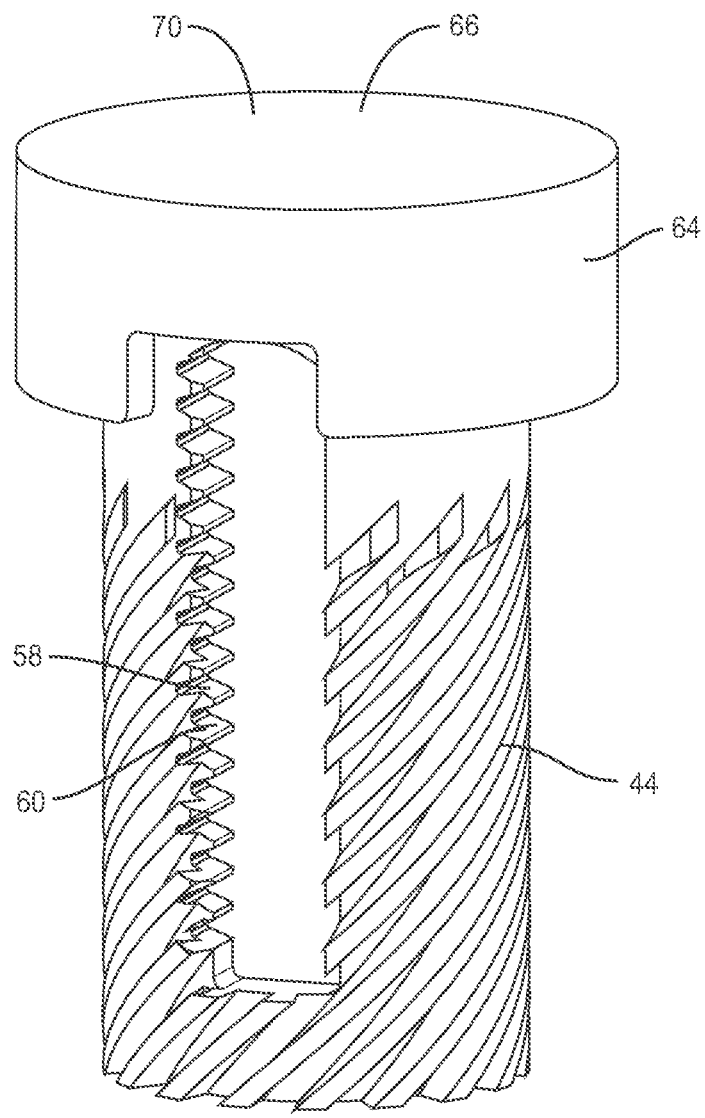
FIG. 3 is a perspective view of components of the system shown in FIG. 1.

Surface 30 includes a portion 36, as shown in FIG. 2, which defines a circumferential cavity 38 disposed adjacent end 24. Portion 36 has a substantially smooth or even surface configuration such that cavity 38 is configured for disposal of a band 40 of implant 20. Band 40 is slidably movable within cavity 38 for rotation relative to portion 36. In some embodiments, portion 36 may be rough, textured, porous, semi-porous, dimpled and/or polished.

Wall 28 defines openings 42 configured to receive an agent, which may include bone graft (not shown) and/or other materials, as described herein, for employment in a fixation or fusion treatment used for example, in connection with a corpectomy. In one embodiment, the agent may include therapeutic polynucleotides or polypeptides and bone growth promoting material, which can be packed or otherwise disposed on or about the surfaces of the components of system 10, including implant 20. The agent may also include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as hydroxyapatite, calcium phosphate and calcium sulfite, biologically active agents, for example, biologically active agents coated onto the exterior of implant 20 and/or applied thereto for gradual release such as by blending in a bioresorbable polymer that releases the biologically active agent or agents in an appropriate time dependent fashion as the polymer degrades within the patient. Suitable biologically active agents include, for example, bone morphogenic protein (BMP) and cytokines.

Body 44 has a tubular configuration and is oriented for disposal within axial cavity 32. Body 44 extends in a linear configuration relative to axis A1. In some embodiments, body 44 may extend in alternate configurations, such as, for example, arcuate, offset, staggered and/or angled portions, which may include acute, perpendicular and obtuse.

Body 44 extends between a first end 46 and a second end 48. Body 44 includes a wall, such as, for example, a tubular wall 50. In some embodiments, wall 50 has a cylindrical cross-section. In some embodiments, the cross-sectional geometry of wall 50 may have various configurations, such as, for example, round, oval, oblong, triangular, polygonal having planar or arcuate side portions, irregular, uniform, non-uniform, consistent, variable, horseshoe shape, U-shape or kidney bean shape. In some embodiments, wall 50 includes an outer surface 52 that is smooth or even. In some embodiments, the outer surface may be rough, textured, porous, semi-porous, dimpled and/or polished. Body 44 is configured for disposal with cavity 32 such that walls 28, 50 are concentric with axis A1.

Figure 4:
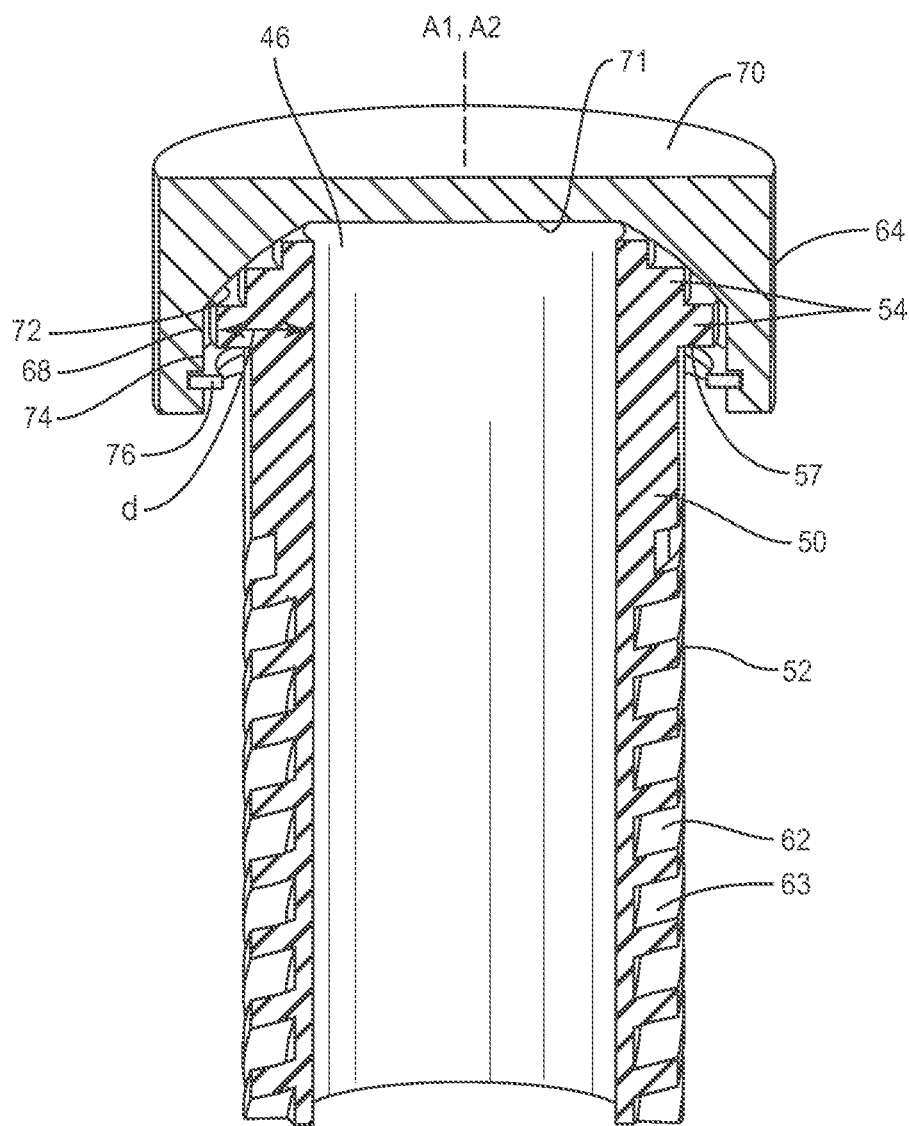
FIG. 4 is a perspective cut away view of components of the system shown in FIG. 1.

A portion of outer surface 52 includes an increasing dimension d of end 46, as shown in FIG. 4. End 46 includes a plurality of steps 54 disposed along dimension d. Steps 54 are configured for engagement with cap 64 to provide selective positioning of cap 64 and to facilitate rotation of the cap relative to axis A1. In some embodiments, end 46 includes one or a plurality of steps 54. In some embodiments, end 46 and/or end 48 can include a surface that may be smooth, rough, textured, porous, semi-porous, dimpled and/or polished such that it facilitates engagement. Steps 54 include an engagement surface 57 that engages a stop 76, discussed below. Engagement surface 57 provides a barrier and/or range of movement for stop 76 such that cap 64 is prevented from rotating beyond selected orientations.

Wall 50 includes an axial opening, such as, for example, an axial slot 56. Slot 56 has a substantially rectangular configuration to facilitate axial translation of body 44 relative to body 22. In some embodiments, slot 56 may have various configurations, such as, for example, round, oval, oblong, triangular, polygonal having planar or arcuate side portions, irregular, uniform or non-uniform. Slot 56 includes a gear rack 58 having a plurality of teeth 60 that are disposed therealong.

A portion of outer surface 52 comprises a helical gear 62 having a plurality of teeth 63 engageable with band 40 to facilitate expansion of implant 20, as described herein. Teeth 63 are spaced apart in a helical configuration and disposed at an angular orientation relative to axis A1 such that body 44 is translatable in a helical gear configuration. In some embodiments, the components of implant 20 may translate to expand implant 20 via engagement of the bodies without a band configuration.

Implant 20 includes a third member, such as, for example, a cap 64. Cap 64 includes an outer surface 66 and an inner surface 68. Surface 66 is configured for engagement with tissue. Surface 66 includes a substantially planar surface 70 oriented transverse to axis A1. In some embodiments, surface 70 can include a surface that may be rough, textured, porous, semi-porous, dimpled and/or polished such that it facilitates engagement with tissue. In some embodiments, surface 70 can include an opening corresponding to the size and cross-section geometry of body 44 to deliver an agent, such as, for example, bone graft to a vertebra endplate.

Cap 64 defines a second axis A2 that is rotatable about and relative to axis A1 and is moveable in a plurality of angular orientations a relative to axis A1, as shown in FIG. 2. Surface 70 is moveable relative to axis A1 with axis A2 between a first angular orientation and a second angular orientation. In one embodiment, surface 70 and axis A2 are moveable through an angular range $\alpha$ of substantially 0 to 20 degrees. In some embodiments, the angular range $\alpha$ may include angle $\alpha 1$ in a range of approximately 0 to 10 degrees. In some embodiments, cap 64 may be disposed with end 46 for relative movement in orientations relative to axis A1, such as, for example, transverse, perpendicular and/or other angular orientations such as acute or obtuse, co-axial and/or may be offset or staggered. In some embodiments, cap 64 may move relative to end 46 in alternate planes relative to a body, such as, for example, vertical, horizontal, diagonal, transverse, coronal and/or sagittal planes of a body. In some embodiments, cap 64 may move relative to end 46 in a multi axial configuration such that cap 64 is rotatable to a selected angle through and within an angular range $\alpha$ relative to axis A1 in a plurality of planes that lie in a cone configuration.

Surface 68 includes a substantially planar surface 71, an angled surface 72 and an annular surface 74. Angled surface 72 is disposed circumferentially about surface 68. Surfaces 71, 72, 74 are configured for engagement with end 46 to facilitate rotation of cap 64 relative to axis A1, as described, to dynamically engage end 46 in response to the engagement of surface 66 with the tissue.

Cap 64 includes a stop 76 disposed with inner surface 68. Stop 76 is configured to define at least one moveable limit of cap 64 relative to body 44 and/or avoid disassembly of the components of implant 20 during insertion with tissue. In one embodiment, the moveable limit includes a plurality of limits, each limit corresponding to one of a plurality of orientations of cap 64 relative to body 44. The intersection between surfaces 71, 72 contacts steps 54 to limit angulation of cap 64.

As instrument I is rotated, body 44 is driven in an axial direction and body 44 axially translates relative to body 22. As gears 56, 62 engage, band 40 slidably rotates within cavity 38 for rotation relative to portion 36 in a configuration to facilitate expansion of implant 20. Body 44 axially translates relative to body 22 and band 40 is disposed therewith between a first, contracted or nested configuration and a second, expanded configuration such that outer body 22 and inner body 44 are disposed to engage adjacent vertebral soft tissue and bone surfaces, as will be described, to restore height and provide support in place of removed vertebrae and/or intervertebral tissue.

Figure 5:
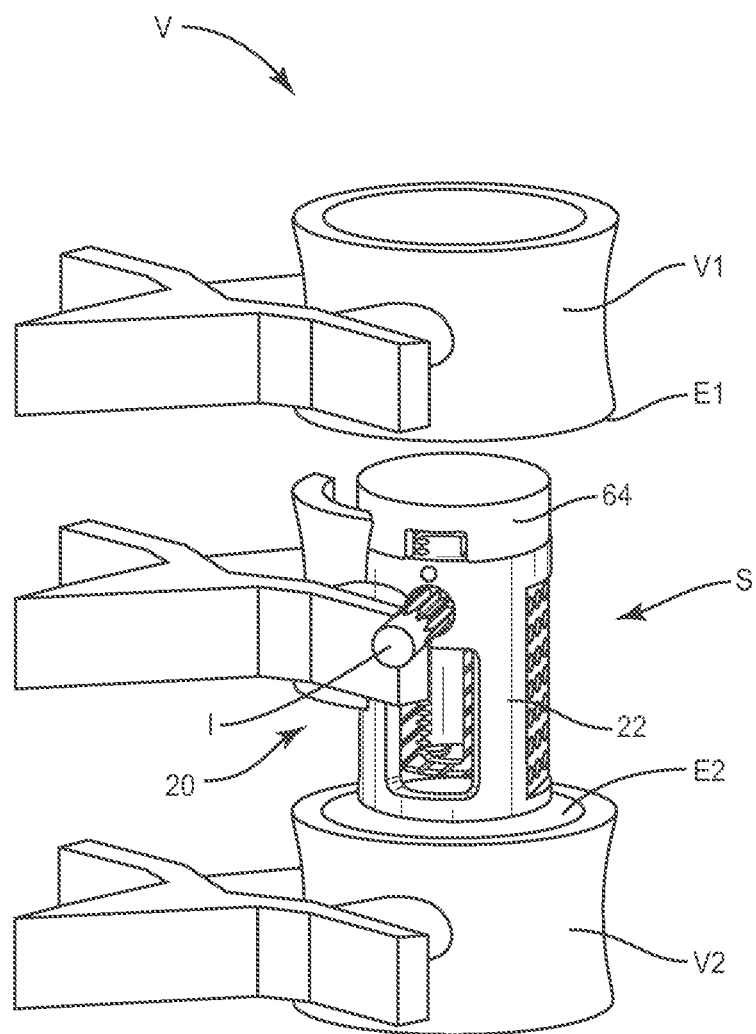
FIG. 5 is a perspective view of components of the system shown in FIG. 1 disposed with vertebrae.

In operation, implant 10 is disposed in a first orientation, as shown in FIGS. 1 and 5, such that body 22 and body 44 are disposed in a concentric configuration with longitudinal axis A1 and disposed in a telescopic arrangement for delivery and implantation adjacent a surgical site. Bodies 22, 44 are seated concentrically such that substantially all of inner body 44 is disposed within outer body 22 in a nested configuration and cap 64 is flush with end 24. When cap 64 is positioned flush with end 24, cap 64 is prevented from rotating so that implant 20 is steady upon insertion between vertebrae. In the first orientation, instrument I is disposed within opening 34 and rotated, in the direction shown by arrow B in FIG. 2, such that instrument I engages teeth 60 for axial translation of body 44 relative to body 22 and rotation of band 40 relative to bodies 22, 44. As instrument I is rotated, in the direction shown by arrow B, instrument I engages teeth 60 to drive body 44 in an axial direction, as shown by arrow C in FIG. 2, and causes axial translation of body 44 relative to body 22 to expand implant 20. In one embodiment, instrument I is rotated, in a direction shown by arrow BB in FIG. 2, such instrument I engages teeth 60 to drive body 44 in an axial direction, as shown by arrow D in FIG. 2, and causes axial translation of body 44 relative to body 22 to contract and/or collapse implant 20 from an expanded configuration, as shown by arrow D in FIG. 2.

Figure 7:
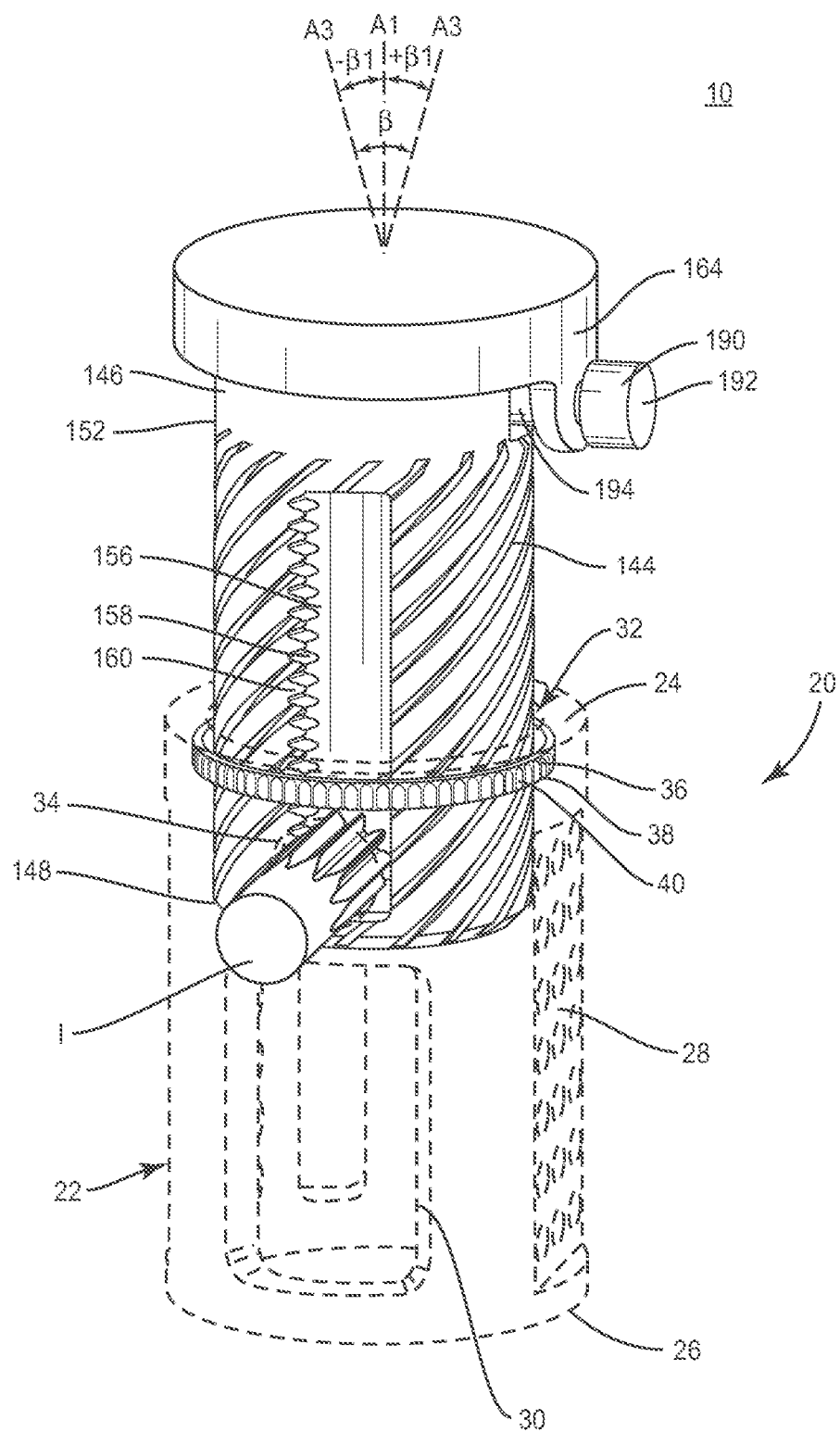
FIG. 7 is a perspective view of components of one embodiment of a surgical system in accordance with the principles of the present disclosure.

As instrument I is rotated in the direction shown by arrow B in FIG. 2, body 44 axially translates, in the direction shown by arrow C in FIG. 2, relative to body 22 such that band 40 slidably rotates within cavity 38 to facilitate expansion of implant 20. Body 44 axially translates relative to body 22 to a second, expanded orientation, as shown in FIGS. 2 and 7, such that outer body 22 and cap 64 are disposed to engage adjacent vertebral soft tissue and bone surfaces, as will be described, to restore height and provide support in place of removed vertebrae and/or intervertebral tissue.

Implant 20 is configured for axial expansion along axis A1. In one embodiment, implant 20 may expand in an arcuate configuration along a curvature relative to axis A1. In some embodiments, all or only a portion of implant 20 may be arcuately expanded, such as one or all of bodies 22, 44 may include a curvature relative to longitudinal axis A1.

In one embodiment, implant 20 is expanded to the second orientation at a selected amount of spacing and/or distraction between vertebrae such that cap 64 engages a first vertebral surface and end 26 engages a second vertebral surface to restore vertebral spacing and provide distraction and/or restore mechanical support function. In one embodiment, implant 20 is expanded, as discussed herein, progressively and/or gradually to provide an implant configured to adapt to the growth of a patient including the vertebrae. In some embodiments, the height of implant 20 may also be decreased over a period of time and/or several procedures to adapt to various conditions of a patient.

In one embodiment, implant 20 is configured for continuous expansion, which includes incremental expansion due to the configuration and dimension, and resulting engagement of instrument I and teeth 60. In some embodiments, incremental expansion may include discrete increments of a particular linear dimension. In some embodiments, the increments of linear dimension may include a range of approximately 0.1-1.0 mm.

Figure 6:
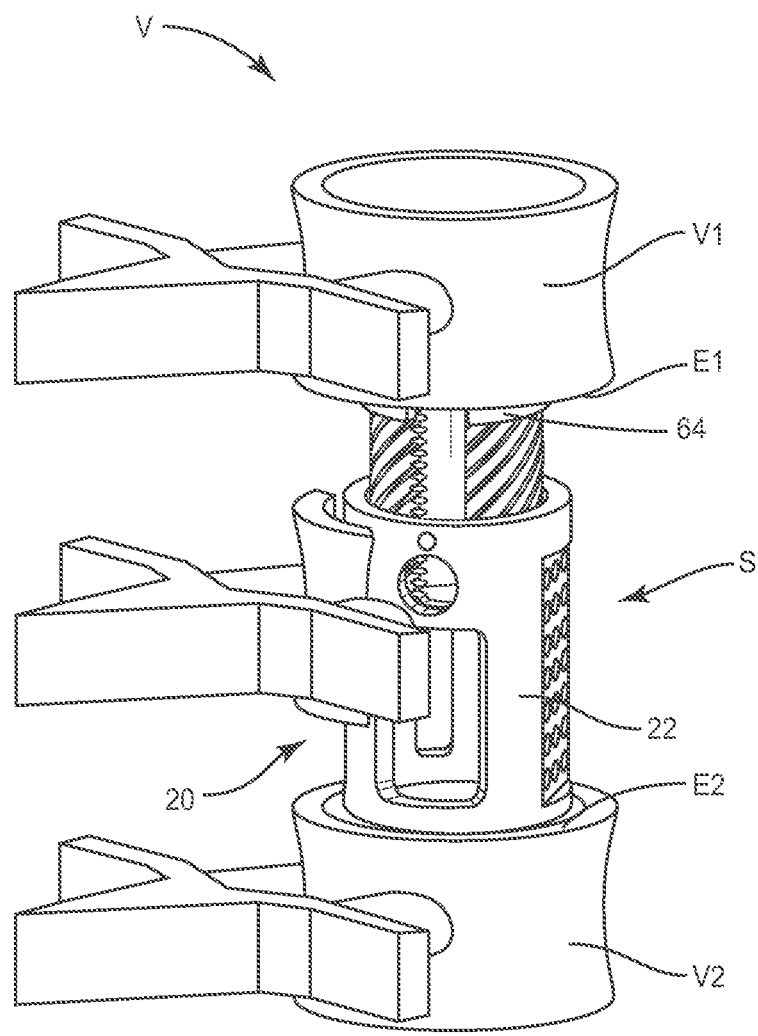
FIG. 6 is a perspective view of components of the system shown in FIG. 1 disposed with vertebrae.

As shown in FIG. 6, as body 44 expands, as discussed above, cap 64 engages vertebrae V1. Cap 64 dynamically engages vertebrae V1 such that as surface 66 engages vertebrae V1, axis A2 of cap 64 rotates relative to and about axis A1 at an angle α, as shown in FIG. 2. Rotation of cap 64 allows surface 66 to adjust its angle to accommodate the specific angle of vertebrae V1. As cap 64 rotates, surfaces 71 and 72 translate about end 46 to accommodate the angle changes of surface 66. Stop 76 provides a range of movement limit and resists and/or prevents cap 64 from rotating about axis A1 beyond a selected limitation of movement of cap 64. The intersection between surfaces 71, 72 contacts steps 54 to limit angulation of cap 64. Stop 76 is configured to engage surface 57 to prevent cap 64 from rotation.

In some embodiments, implant 20 provides a footprint that improves stability and decreases the risk of subsidence into tissue. In some embodiments, implant 20 provides height restoration between vertebral bodies, decompression, restoration of sagittal and/or coronal balance and/or resistance of subsidence into vertebral endplates.

Referring to FIGS. 5 and 6, in assembly, operation and use, system 10 including implant 20, similar to that described with regard to FIGS. 1-4, is employed with a surgical procedure, such as, for example, a lumbar corpectomy for treatment of a spine of a patient including vertebrae V. System 10 may also be employed with other surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners for securement of implant 20.

System 10 is employed with a lumbar corpectomy including surgical arthrodesis, such as, for example, fusion to immobilize a joint for treatment of an applicable condition or injury of an affected section of a spinal column and adjacent areas within a body. For example, vertebrae V includes a first vertebra V1 and a second vertebra V2. A diseased and/or damaged vertebra and intervertebral discs are disposed between the vertebrae V1 and V2. In some embodiments, system 10 is configured for insertion with a vertebral space to space apart articular joint surfaces, provide support and maximize stabilization of vertebrae V.

In use, to treat the affected section of vertebrae V, a medical practitioner obtains access to a surgical site including vertebrae V in any appropriate manner, such as through incision and retraction of tissues. In some embodiments, system 10 may be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, corpectomy is performed for treating the spine disorder. The diseased and/or damaged portion of vertebrae V, and diseased and/or damaged intervertebral discs are removed to create a vertebral space S.

A preparation instrument (not shown) is employed to remove disc tissue, fluids, adjacent tissues and/or bone, and scrape and/or remove tissue from endplate surfaces E1 of vertebra V1 and/or endplate surface E2 of vertebra V2. Implant 20 is provided with at least one agent, similar to those described herein and as described above, to promote new bone growth and fusion to treat the affected section of vertebrae V.

Implant 10 is disposed in a first orientation, as shown in FIG. 5 and described above with regard to FIGS. 1-4, such that body 22 and body 44 are disposed in a concentric configuration with axis A1 and disposed in a telescopic arrangement for delivery and implantation adjacent a surgical site. Bodies 22, 44 are seated concentrically such that substantially all of inner body 44 is disposed within outer body 22 in a nested configuration and cap 64 is flush with end 24.

Implant 20 is delivered to the surgical site adjacent vertebrae V with a delivery instrument (not shown) including a driver via the protected passageway for the arthrodesis treatment. The driver delivers implant 20 into the prepared vertebral space S, between vertebra V1 and vertebra V2, according to the requirements of a particular surgical application. Implant 20 is manipulated such that end 26 engages endplate surface E2. A gripping surface of end 26 penetrates and fixes with endplate surface E2. Implant 20 is positioned in the first orientation with endplate surface E2.

In the first orientation, instrument I is disposed within opening 34 and rotated, in the direction shown by arrow B in FIG. 2, such that instrument I engages teeth 60 for axial translation of body 44 relative to body 22 and rotation of band 40 relative to bodies 22, 44. As instrument I is rotated, in the direction shown by arrow B, instrument I engages teeth 60 to drive body 44 in an axial direction, as shown by arrow C in FIG. 2, and cause axial translation of body 44 relative to body 22 to expand implant 20 to a second orientation, as shown in FIG. 6. As such, implant 20 expands within vertebral space S and cap 64 engages endplate surface E1. Surface 66 fixes with endplate surface E1. In one embodiment, instrument I is rotated, in a direction shown by arrow BB in FIG. 2, such that instrument I engages teeth 60 to drive body 44 in an axial direction, as shown by arrow D in FIG. 2, and cause axial translation of body 44 relative to body 22 to contract and/or collapse implant 20 from an expanded configuration.

Cap 64 dynamically engages vertebra V1 such that surface 66 engages vertebra V1 and axis A2 rotates about axis A1 at angle α, as shown in FIG. 2. Rotation of cap 64 allows surface 66 to selectively adjust its angle to accommodate the specific angle of vertebra V1. As cap 64 rotates, surfaces 71 and 72 translate about end 46 to accommodate the angle changes of surface 66. The intersection between surfaces 71, 72 contacts steps 54 to limit angulation of cap 64. Stop 76 prevents cap 64 from rotating about axis A1, as described.

Implant 20 engages and spaces apart opposing endplate surfaces E1, E2 and is secured within vertebral space S to stabilize and immobilize portions of vertebrae V in connection with bone growth for fusion and fixation of vertebrae V1, V2. Fixation of implant 20 with endplate surfaces E1, E2 may be facilitated by the resistance provided by the joint space and/or engagement with endplate surfaces E1, E2. A lock can be provided to prevent body 44 from axially translating relative to body 22 to fix implant 20 in a selected expanded and/or contracted orientation, including those described herein.

In some embodiments, implant 20 may engage only one endplate. In some embodiments, an agent(s), as described herein, may be applied to areas of the surgical site to promote bone growth. Components of system 10 including implant 20 can be delivered or implanted as a pre-assembled device or can be assembled in situ. Components of system 10 including implant 20 may be completely or partially revised, removed or replaced in situ. In some embodiments, one or all of the components of system 10 can be delivered to the surgical site via mechanical manipulation and/or a free hand technique.

In one embodiment, implant 20 may include fastening elements, which may include locking structure, configured for fixation with vertebrae V1, V2 to secure joint surfaces and provide complementary stabilization and immobilization to a vertebral region. In some embodiments, locking structure may include fastening elements such as, for example, rods, plates, clips, hooks, adhesives and/or flanges. In some embodiments, system 10 can be used with screws to enhance fixation. In some embodiments, system 10 and any screws and attachments may be coated with an agent, similar to those described herein, for enhanced bony fixation to a treated area. The components of system 10 can be made of radiolucent materials such as polymers. Radiomarkers may be included for identification under x-ray, fluoroscopy, CT or other imaging techniques.

In one embodiment, system 10 includes a plurality of implants 20. In some embodiments, employing a plurality of implants 20 can optimize the amount vertebral space S can be spaced apart such that the joint spacing dimension can be preselected. The plurality of implants 20 can be oriented in a side by side engagement, spaced apart and/or staggered.

In some embodiments, the use of microsurgical and image guided technologies may be employed to access, view and repair spinal deterioration or damage, with the aid of system 10. Upon completion of the procedure, the non-implanted components, surgical instruments and assemblies of system 10 are removed and the incision is closed.

Figure 8:
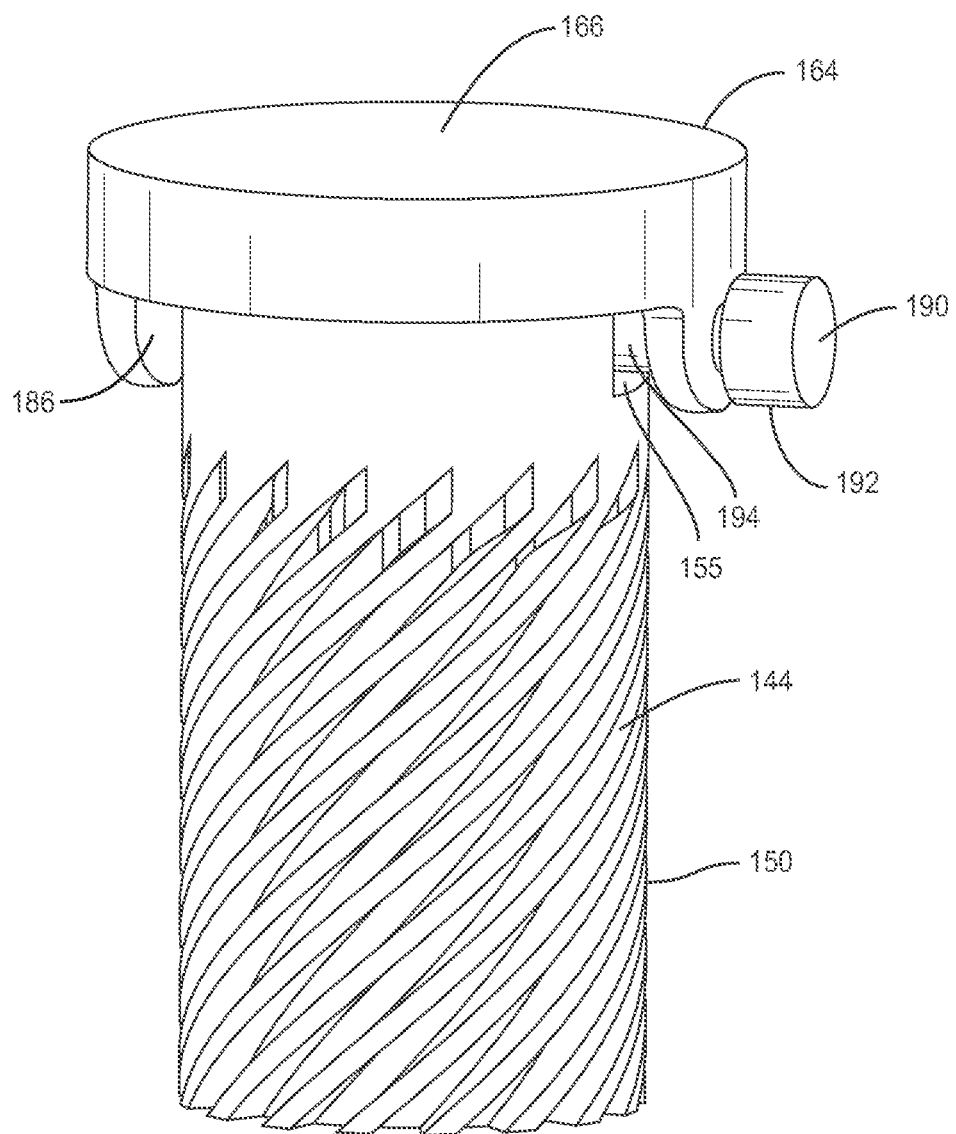
FIG. 8 is a perspective view of components of the system shown in FIG. 7.
Figure 9:
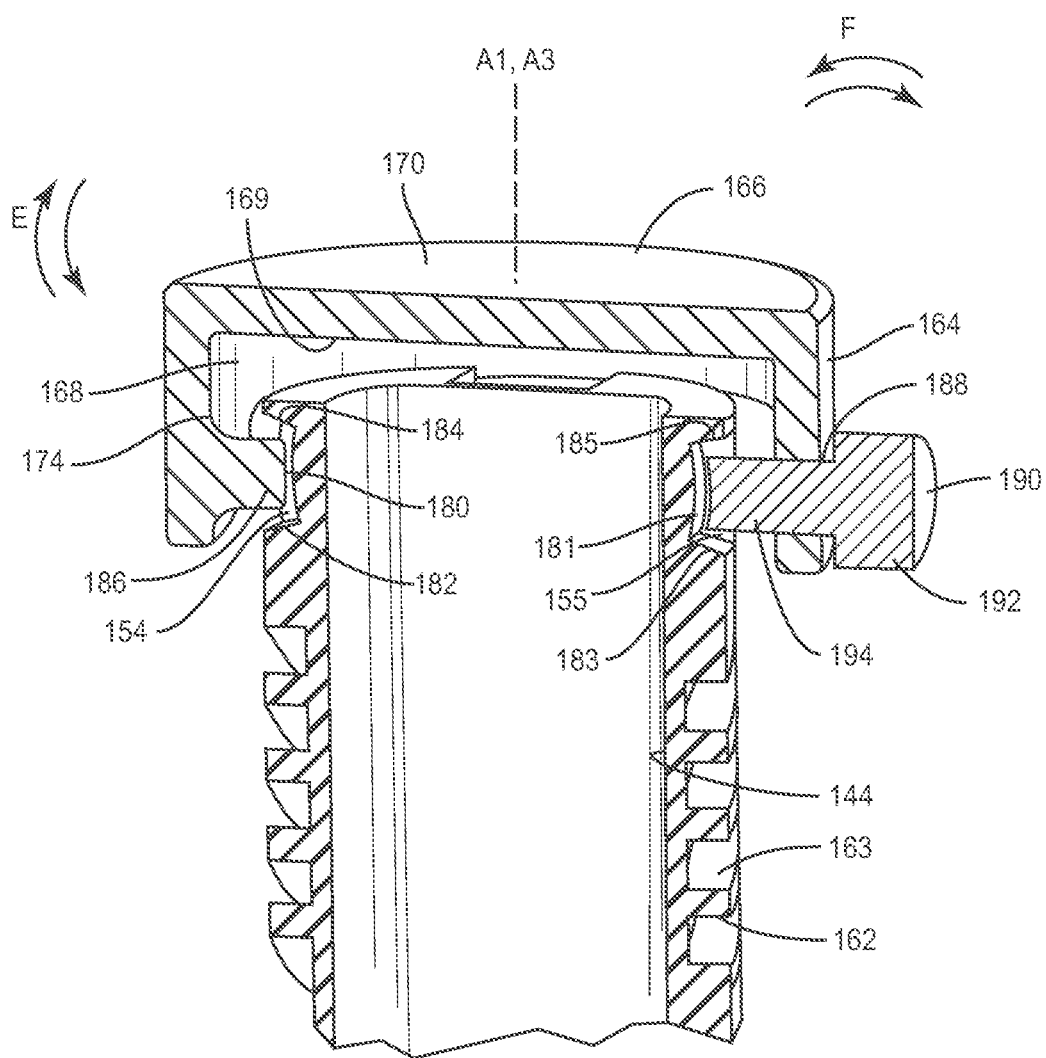
FIG. 9 is a cut away view of the components of the system shown in FIG. 7.

In one embodiment, as shown in FIGS. 7-9, system 10 includes implant 20, similar to that described above with regard to FIGS. 1-6, having outer body 22, described above, and an inner body 144. Body 144 has a tubular configuration and is oriented for disposal within axial cavity 32. Body 144 extends in a linear configuration relative to axis A1. Body 144 extends between a first end 146 and a second end 148. Body 144 includes a wall, such as, for example, a tubular wall 150. Body 144 is configured for disposal with cavity 32 such that walls 28, 150 are concentric with axis A1.

A portion of outer surface 152 at end 146 defines at least one cavity 154. Cavity 154 is configured for moveable disposal of a cap 164, as discussed below. Cavity 154 facilitates the dynamic engagement of cap 164 and end 146. In one embodiment, implant 20 includes two cavities 154, 155. Cavities 154, 155 each include surfaces 180, 181 that are substantially spherical and surfaces 182, 183 and 184, 185 each being transverse to axis A1. In some embodiments, surfaces 180, 181, 182, 183, 184, 185 can include a surface that may be smooth, rough, textured, porous, semi-porous, dimpled and/or polished such that it facilitates engagement. Surfaces 180, 181, 182, 183, 184, 185 are configured as stop limits to restrict movement of cap 164.

Wall 150 includes an axial slot 156. Slot 156 has a substantially rectangular configuration to facilitate axial translation of body 144 relative to body 22. Slot 156 includes a gear rack 158 having a plurality of teeth 160 that are disposed therealong.

A portion of outer surface 152 comprises a helical gear 162 having a plurality of teeth 163 engageable with band 40 to facilitate expansion of implant 20, as described herein. Teeth 163 are spaced apart in a helical configuration and disposed at an angular orientation relative to axis A1 such that body 144 is translatable in a helical gear configuration.

Implant 20 includes a third member, such as, for example, cap 164. Cap 164 includes an outer surface 166 and an inner surface 168. Surface 166 is configured for engagement with tissue. Surface 166 includes a substantially planar surface 170 oriented transverse to axis A1. Cap 164 includes a post 186 disposed on one side of cap 164. Post 186 extends into and is movably disposed with cavity 154. Cap 164 includes an opening 188 extending between surfaces 166 and 168. Opening 188 is configured to receive a moveable post 190. Post 190 includes a knob portion 192 and a stem portion 194. Stem portion 194 is configured for moveable disposal in cavity 155. Posts 186 and 190 facilitate rotational movement of cap 164, in the directions shown by arrows E in FIG. 9. Cavities 154, 155 facilitate rotation of cap 164, in the directions shown by arrows F in FIG. 9.

Cap 164 defines an axis A3 that is moveable in a plurality of axial angular orientations β relative to axis A1 as shown in FIG. 7. Surface 170 is moveable relative to axis A1 with axis A2 between a first angular orientation and a second angular orientation. In one embodiment, the angular range β of substantially 0 to 20 degrees. In some embodiments, angle β1 may include a range of approximately 0 to 10 degrees. In some embodiments, cap 164 may be disposed with end 146 for relative movement in orientations relative to axis A1, such as, for example, transverse, perpendicular and/or other angular orientations such as acute or obtuse, co-axial and/or may be offset or staggered. In some embodiments, cap 164 may move relative to end 146 in alternate planes relative to a body, such as, for example, vertical, horizontal, diagonal, transverse, coronal and/or sagittal planes of a body. In some embodiments, cap 164 may move relative to end 46 in a multi axial configuration such that cap 164 is rotatable to a selected angle through and within an angular range α relative to axis A1 in a plurality of planes that lie in a cone configuration.

Surface 168 includes a substantially planar surface 169 and an annular surface 174. Surfaces 169, 174 are configured for engagement with end 146 to facilitate rotation of cap 164 relative to axis A1 to dynamically engage end 146 in response to the engagement of outer surface 166 with the tissue.

Movement of cap 164 is limited by surfaces 180, 181, 182, 183, 184, 185 of cavities 154, 155. As cap 164 rotates, post 186 translates along surface 180 until it contacts either surface 182 or 184. When post 186 contacts either surface 182, 184, it prevents further rotation of cap 164. As cap 164 rotates, post 194 translates along surface 181 until it contacts either surface 183 or 185. When post 194 contacts either surface 183, 185, it resists and/or prevents rotation of cap 164.

Cap 164 dynamically engages vertebrae such that as surface 166 engages vertebrae, axis A3 rotates relative to axis A1 at angle β, as shown in FIG. 7. Rotation of cap 164 allows surface 166 to selectively adjust its angle to accommodate the specific angle of the vertebrae. As cap 164 rotates, surfaces 169 and 174 translate about end 146 to accommodate the angle changes of surface 166. Cavities 154, 155 resist and/or prevent cap 164 from rotating about axis A4 to providing limitations on movement of cap 164.

Figure 10:
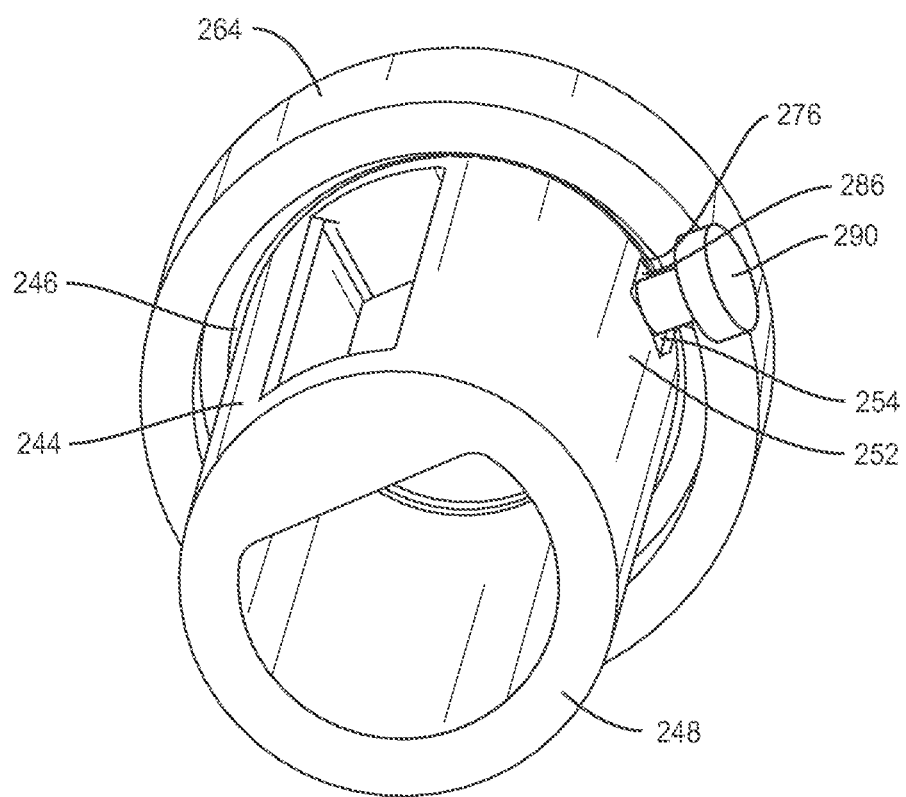
FIG. 10 is a perspective view of components of one embodiment of a surgical system in accordance with the principles of the present disclosure.

In one embodiment, as shown in FIG. 10, system 10 includes implant 20, similar to the systems and methods described above, includes an inner body 244. Body 244 extends between a first end 246 and a second end 248. Body 244 includes a cap 264. Cap 264 includes a stop 276, similar to stop 76 described above. A portion of outer surface 252 at end 246 defines at least one cavity 254. Cavity 254 is configured for moveable disposal of cap 264, as discussed above. Cavity 254 facilitates dynamic engagement of cap 264 and end 246. Cap 264, similar to cap 64 described above, is an articulating end cap that adjusts to match an orientation of vertebral endplates and selectively determines the orientation, such as, for example a required angle, of cap 264 for engagement with the vertebral endplates. This configuration facilitates distribution of a compressive load of vertebrae and can accommodate for axial offset in a sagittal and/or a coronal plane of a body, similar to that described herein. Cap 264 includes a post 286, similar to post 186, disposed on at least one side of cap 264. Post 286 extends into and is movably disposed with cavity 154 to facilitate and limit movement of cap 264, as discussed above. This configuration facilitates two distinct degrees of freedom to allow for articulation of cap 264 relative to end 246.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method comprising:
   inserting an implant into a vertebral space; and
   expanding the implant within the intervertebral space, wherein the implant comprises:
     an inner member extending between a first end and a second end and defining a longitudinal axis, the inner member including a cavity,
     a cap including a top wall and a side wall extending from the top wall, the side wall including opposite inner and outer surfaces, the outer surface defining a perimeter of the cap, and
     a post coupled to the cap, the post having a first end movably disposed in the cavity and an opposite second end positioned outside of the perimeter,
   wherein the cavity is defined by an arcuate first surface of the inner member that is positioned between second and third surfaces of the inner member, the first, second and third surfaces each defining a stop limit that restricts movement of the cap relative to the inner member.

2. The method recited in claim 1, wherein inserting the implant into the vertebral space comprises engaging the second end with an endplate of a vertebra such that a gripping surface of the second end penetrates the endplate.

3. The method recited in claim 1, wherein:
   the implant includes an outer member, the inner member being positioned within the outer member; and
   expanding the implant within the intervertebral space comprises rotating the inner member relative to the outer member.

4. The method recited in claim 1, wherein:
   the implant includes an outer member, the inner member being positioned within the outer member; and
   expanding the implant within the intervertebral space comprises inserting an instrument through the outer member such that the instrument engages teeth of the inner member and rotation of the instrument translates the inner member relative to the outer member along the longitudinal axis.

5. The method recited in claim 1, wherein:
   the implant includes an outer member and a band, the inner member being positioned within the outer member such that the band is positioned in a cavity of the outer member and between the inner member and the outer member; and
   expanding the implant within the intervertebral space comprises inserting an instrument through the outer member such that the instrument engages teeth of the inner member and rotation of the instrument translates the inner member relative to the outer member along the longitudinal axis such that the band slidably rotates within the cavity.

6. The method recited in claim 1, wherein:
   the implant includes an outer member and a band, the inner member being positioned within the outer member such that the band is positioned in a cavity of the outer member and a helical groove of the inner member; and
   expanding the implant within the intervertebral space comprises inserting an instrument through the outer member such that the instrument engages teeth of the inner member and rotation of the instrument translates the inner member relative to the outer member along the longitudinal axis such that the band slidably rotates within the cavity and translates within a helical groove.

7. The method recited in claim 1, wherein expanding the implant within the intervertebral space comprises moving the implant from a first orientation in which the cap is spaced apart from a superior vertebra to a second orientation in which the cap directly engages the superior vertebra.

8. The method recited in claim 1, wherein expanding the implant within the intervertebral space comprises engaging the top wall with a vertebra to move the cap relative to the inner member from a first orientation in which the top surface extends perpendicular to the longitudinal axis to a second orientation in which the top surface extends at an acute angle relative to the longitudinal axis.

9. The method recited in claim 1, wherein expanding the implant within the intervertebral space comprises engaging the top wall with a vertebra to move the cap relative to the inner member from a first orientation in which the top surface extends at an acute angle relative to an endplate of the vertebra to a second orientation in which the top surface extends parallel to the endplate.

10. The method recited in claim 1, wherein expanding the implant within the intervertebral space comprises engaging the implant with endplates of vertebrae to secure the implant within the intervertebral space and immobilize portions of the vertebrae.

11. The method recited in claim 1, wherein:
    the implant includes an outer member, the inner member being positioned within the outer member; and
    the further comprises locking the implant to prevent the inner member from translating relative to the outer member.

12. The method recited in claim 1, wherein the post is fixed relative to the cap.

13. The method recited in claim 1, wherein the post is monolithically formed with the cap.

14. The method recited in claim 1, wherein the cap defines a first axis movable in a plurality of axial orientations relative to the longitudinal axis.

15. The method recited in claim 1, wherein the top wall includes a substantially planar surface oriented transverse to the longitudinal axis and movable relative to an orientation of the tissue.

16. The method recited in claim 15, wherein the planar surface is movable relative to the longitudinal axis in an angular range of substantially 0 to 20 degrees.

17. The method recited in claim 1, wherein first and second ends of the post each have a cylindrical cross-section, the second end of the post having a diameter greater than a diameter of the first end of the post.

18. A method comprising:
inserting an implant into a vertebral space; and
expanding the implant within the intervertebral space, wherein the implant comprises:
an inner member extending between a first end and a second end and defining a longitudinal axis, the inner member including a cavity,
a cap including a top wall and a side wall extending from the top wall, the side wall including opposite inner and outer surfaces, the outer surface defining a perimeter of the cap, and
a post coupled to the cap, the post having a first end movably disposed in the cavity and an opposite second end positioned outside of the perimeter,
wherein the implant includes an outer member and a band, the inner member being positioned within the outer member such that the band is positioned in a cavity of the outer member and between the inner member and the outer member, and
wherein expanding the implant within the intervertebral space comprises inserting an instrument through the outer member such that the instrument engages teeth of the inner member and rotation of the instrument translates the inner member relative to the outer member along the longitudinal axis such that the band slidably rotates within the cavity.

19. The method recited in claim 18, wherein inserting the implant into the vertebral space comprises engaging the second end with an endplate of a vertebra such that a gripping surface of the second end penetrates the endplate.

20. A method comprising:
inserting an implant into a vertebral space; and
expanding the implant within the intervertebral space, wherein the implant comprises:
an inner member extending between a first end and a second end and defining a longitudinal axis, the inner member including a cavity,
a cap including a top wall and a side wall extending from the top wall, the side wall including opposite inner and outer surfaces, the outer surface defining a perimeter of the cap, and
a post coupled to the cap, the post having a first end movably disposed in the cavity and an opposite second end positioned outside of the perimeter,
wherein the implant includes an outer member and a band, the inner member being positioned within the outer member such that the band is positioned in a cavity of the outer member and a helical groove of the inner member, and
wherein expanding the implant within the intervertebral space comprises inserting an instrument through the outer member such that the instrument engages teeth of the inner member and rotation of the instrument translates the inner member relative to the outer member along the longitudinal axis such that the band slidably rotates within the cavity and translates within a helical groove.

* * * * *